United States Patent
Czarnek

(10) Patent No.: US 7,468,789 B2
(45) Date of Patent: Dec. 23, 2008

(54) FLOW CYTOMETER FOR RAPID BACTERIA DETECTION

(75) Inventor: Robert Czarnek, Johnstown, PA (US)

(73) Assignee: Advanced Analytical Technologies, Inc., Ames, IA (US)

( * ) Notice: Subject to any disclaimer, the term of this patent is extended or adjusted under 35 U.S.C. 154(b) by 205 days.

(21) Appl. No.: 11/051,871

(22) Filed: Feb. 4, 2005

(65) Prior Publication Data

US 2005/0174572 A1   Aug. 11, 2005

Related U.S. Application Data

(60) Provisional application No. 60/542,188, filed on Feb. 5, 2004.

(51) Int. Cl.
*G01N 1/10* (2006.01)
*G01N 21/01* (2006.01)

(52) U.S. Cl. .................... 356/246; 356/244
(58) Field of Classification Search .......... 356/244–246
See application file for complete search history.

(56) References Cited

U.S. PATENT DOCUMENTS

| | | | |
|---|---|---|---|
| 3,871,770 A | 3/1975 | von Behrens et al. | |
| 4,343,551 A | 8/1982 | Eisert | |
| 4,352,558 A * | 10/1982 | Eisert | 356/39 |
| 4,660,971 A | 4/1987 | Sage et al. | |
| 4,983,038 A | 1/1991 | Ohki et al. | |
| 4,988,619 A | 1/1991 | Pinkel | |
| 5,311,290 A * | 5/1994 | Olson et al. | 356/634 |
| 5,414,508 A * | 5/1995 | Takahashi et al. | 356/246 |
| 5,480,775 A * | 1/1996 | Ito et al. | 435/7.2 |
| 5,985,216 A * | 11/1999 | Rens et al. | 422/73 |
| 6,473,171 B1 * | 10/2002 | Buttry et al. | 356/246 |
| 2002/0141902 A1 * | 10/2002 | Ozasa et al. | 422/82.09 |
| 2004/0070757 A1 * | 4/2004 | Moore et al. | 356/339 |

FOREIGN PATENT DOCUMENTS

WO   WO0148455   *   7/2001

* cited by examiner

*Primary Examiner*—Tarifur Chowdhury
*Assistant Examiner*—Tara S Pajoohi
(74) *Attorney, Agent, or Firm*—The Webb Law Firm

(57) ABSTRACT

A cytometer system includes a fluid input manifold having a sample bore for accommodating a flow of sample fluid surrounded by a frustoconical shaped chamber for accommodating a flow of sheath fluid. A cuvette has a central bore positioned for receiving from the sample bore the flow of the sample fluid surrounded by and in non-mixing contact with the flow of the sheath fluid. The section of the central bore receiving the sample fluid and the sheath fluid has a frustoconical shape that converges and terminates in a section of the central bore that has a square cross section.

21 Claims, 8 Drawing Sheets

FLOW CYTOMETER FOR RAPID BACTERIA DETECTION

CROSS REFERENCE TO RELATED APPLICATIONS

The present application claims priority from U.S. Provisional Application No. 60/542,188, filed Feb. 5, 2004, which is incorporated herein by reference.

FIELD OF THE INVENTION

The present invention relates to a system for detecting contaminants in a liquid and, more particularly, to a system for detecting and measuring low levels of bacteria in the liquid.

DESCRIPTION OF RELATED ART

Cytometer systems are well known in the art for counting individual, micron-size particles (bacteria, yeast, etc.) as they pass through a beam of laser light. A single-file flow of particles is achieved by using an effect known as hydrodynamic focusing. Specifically, particles that have been tagged with a dye are suspended in a sample fluid. The sample fluid containing the suspended particles is delivered to a flow cell, comprised of a cuvette, via a fluid input manifold.

Hydrodynamic focusing is achieved by passing a higher velocity "sheath" of fluid around the interior of the cuvette whereupon the sample fluid containing the particles under test become entrained in the sheath fluid. The sample fluid containing the particles under test is confined to the central region of the sheath flow creating a sample core. Various fluorescent dyes can provide information on the viability state of microbes for quantification and identification. In addition to scattering the laser light, labeled microbes will also fluoresce. Quantification is achieved through the photoelectric effect by counting the number of photons admitting at both fluorescence and scattered laser light wavelengths whose intensities meet the calibration criteria for a developed method.

The present invention is a cytometer system having an improved laser optics focusing system, an improved optical system for detecting scattered laser light as well as laser-induced fluorescence produced by interaction between particles in the sample flow with the focused laser light, and an improved system for delivering sample fluid and sheath fluid to the cuvette.

SUMMARY OF THE INVENTION

The invention is a cytometer system comprising a fluid input manifold having a sample bore defining a first end for receiving a sample fluid therein and a second end for discharging the received sample fluid. The fluid input manifold also has an injection chamber surrounding the sample bore in spaced relation thereto. The injection chamber has a first end for receiving sheath fluid therein and a second end for discharging the received sheath fluid. The injection chamber has a cross section that gradually decreases in area toward the second end thereof. The system also includes an elongated cuvette having a central bore. The first end of the central bore is positioned for receiving from the input manifold a flow of sample fluid surrounded by a flow of sheath fluid and a second end for discharging the received fluids. The first end of the central bore has a cross section that gradually diminishes in diameter with increasing distance away from the first end thereof. This gradually diminishing cross-sectional diameter of the central bore terminates in a length of the central bore that extends toward the second end of the central bore.

Desirably, the manifold has two surfaces positioned in spaced relation to define the injection chamber, which, desirably, is frustoconical shaped.

The fluid input manifold can include a first body part that has a cone shaped projection extending therefrom. The cone shaped projection can have the sample bore extending therethrough. The fluid input manifold can also include a second body part that has a cone shaped aperture therein. The first and second body parts can be configured to mate such that the cone shaped projection is received in spaced relation to the cone shaped aperture thereby defining the injection chamber.

The first body part can include a groove surrounding a base of the cone shaped projection, whereupon when the first and second body parts are mated, a surface of the second body part partially covers the groove thereby defining a chamber that surrounds the base of the cone shaped projection and is in fluid communication with said first end of said injection chamber around said cone shaped projection.

The first body part can include at least one passage in fluid communication between the groove and a surface of the first body part that is not in contact with the second body part when the first and second body parts are mated. The sample bore can be in fluid communication with a surface of the first body part that is not in contact with the second body part when the first and second body parts are mated.

The second end of the injection chamber has an outside diameter that is smaller than an outside diameter of the first end of the central bore of the cuvette.

The system can include a fluid output manifold having a discharge bore for passage of fluids discharged from the second end of the central bore of the cuvette.

The system can include a frame for supporting the input manifold and the output manifold with the cuvette therebetween such that the sample bore of the input manifold, the central bore of the cuvette and the discharge bore of the output manifold are in alignment.

The system can include a first compression fitting between the first end of the cuvette and the input manifold, and a second compression fitting between the second end of the cuvette and the output manifold. The first and second compression fittings can form fluid tight seals between the first and second ends of the cuvette and the first and second fluid manifolds, respectively.

The system can include means for producing a beam of monochromatic light and an optical system for directing and shaping the beam of light such that its focal point is positioned in a flow of sample fluid surrounded by a flow of sheath fluid in the sample bore. Desirably, the focal point has an elongated shape that is oriented perpendicular to a direction of flow of the sample fluid.

The optical system can include a low power lens positioned in a path of the beam of monochromatic light, a focusing lens coupled to the frame and positioned in the beam of monochromatic light exiting said low power lens, and means for adjusting a position of at least one of the low power lens and the focusing lens to adjust the position of the focal point of the beam of light.

The system can further include a second optical system for focusing light resulting from the interaction of the beam of light with the sample fluid and means for converting the focused light into at least one electrical signal for detection by processing electronics.

The second optical system can include at least one lens for focusing the light produced by the interaction of the shaped beam of light with the sample fluid and at least one spatial filter for filtering the focused light to remove undesirable reflections therefrom. The means for converting the focused light can include at least one photodetector.

The system can further include a beam splitter for directing a first wavelength of focused light to a first photodetector and for directing a second wavelength of focused light to a second photodetector via a band-pass filter which is configured to remove undesirable wavelengths of focused light that accompany the second wavelength of focused light.

The invention is also a cytometer system comprising a fluid input manifold including a sample bore for accommodating a flow of sample fluid surrounded by a frustoconical shaped chamber for accommodating a flow of sheath fluid, and a cuvette including a central bore positioned for receiving from the input manifold the flow of the sample fluid surrounded by and in non-mixing contact with the flow of the sheath fluid. The section of the central bore receiving the sample fluid and the sheath fluid has a frustoconical shape. The frustoconical shaped section of the central bore converges and terminates in a section of the central bore that has a square cross section.

The sheath fluid can exit the frustoconical shaped chamber adjacent the end thereof that has a minimum outside diameter and can enter the frustoconical shaped section of the central bore adjacent the end thereof that has a maximum outside diameter. Desirably, the maximum outside diameter of the frustoconical shaped section of the central bore is the same as the minimum outside diameter of the frustoconical shaped chamber.

The input manifold can include a pre-injection chamber in fluid communication with an end of the frustoconical shaped chamber opposite the cuvette. The pre-injection chamber and the end of the frustoconical shaped chamber opposite the cuvette can be configured whereupon sheath fluid input into the pre-injection chamber drains gradually into the end of the frustoconical shaped chamber opposite the cuvette.

Desirably, at least one of the sample fluid and the sheath fluid is introduced into the input manifold at a controlled rate.

DETAILED DESCRIPTION OF THE INVENTION

Figure 1:
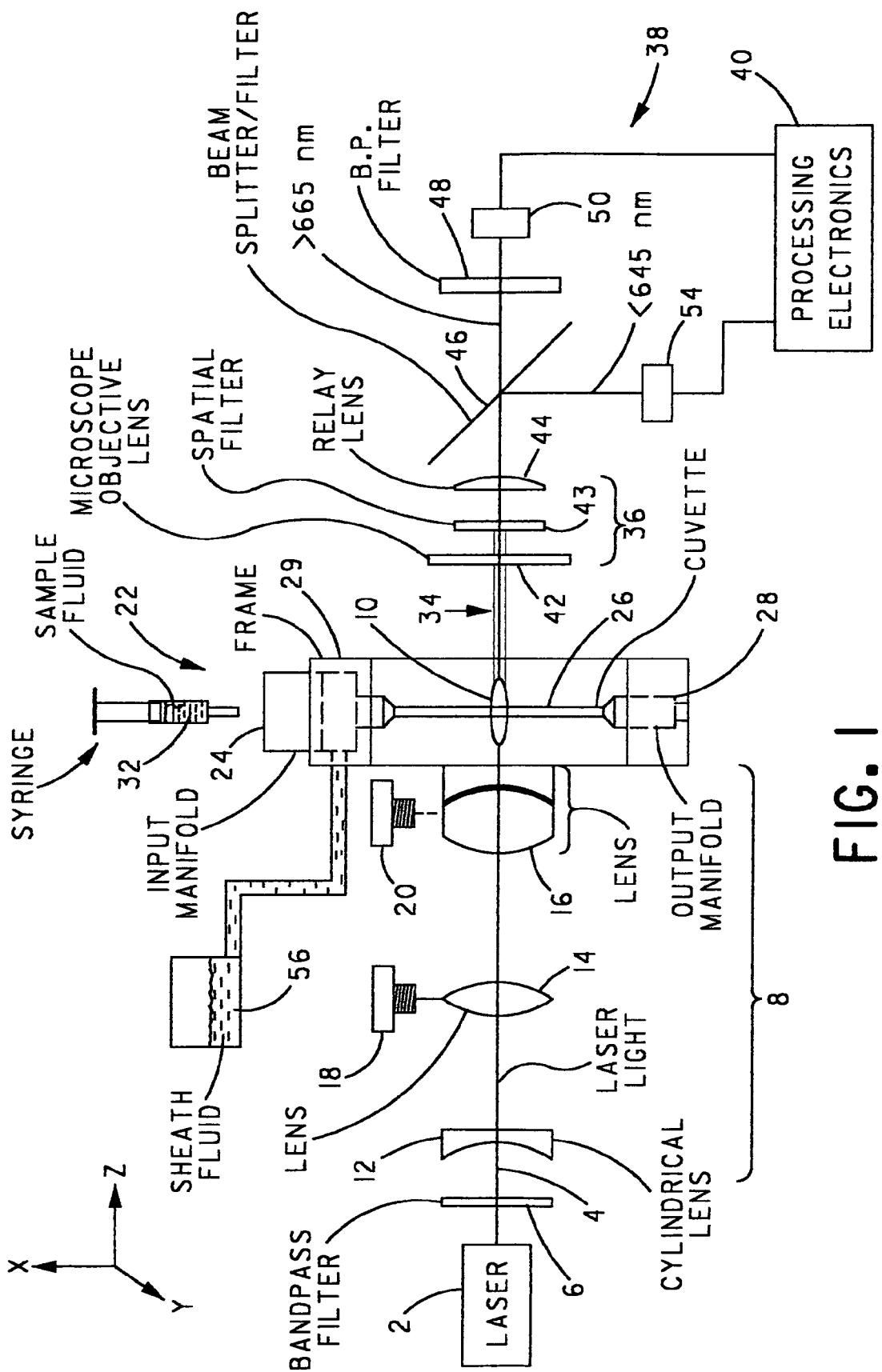
FIG. 1 is a diagrammatic illustration of a cytometer system in accordance with the present invention.

The present invention will be described with reference to the accompanying figures where like reference numbers correspond to like elements.

A cytometer system in accordance with the present invention includes means, such as a laser 2, for outputting a beam of monochromatic light, such as laser light 4. Laser light 4 exiting laser 2 passes through a band-pass filter 6 which eliminates unwanted wavelengths from laser light 4. In one non-limiting embodiment laser light exiting band-pass filter 6 has a wavelength of 635 nm±10 nm. Laser light 4 exiting band-pass filter 6 passes through a beam shaping and focusing optical system 8 which directs and shapes laser light 4 such that it has an elongated shape at its focal point 10. Desirably, optical system 8 includes in series between band-pass filter 6 and focal point 10 a cylindrical lens 12, a low power positive or negative lens 14 and a focusing lens 16. Lens 14 can be biased against an adjustment stage 18 which can be utilized to adjust the X, Y and/or Z positions of lens 14 with respect to lens 16. Also or alternatively, lens 16 can be biased against an adjustment stage 20 which can be utilized for adjusting the X, Y and/or Z positions of lens 16 with respect to lens 14.

The cytometer system also includes a sample flow system 22 comprised of a fluid input manifold 24, a cuvette 26 (such as, without limitation, a square bore tube) and a fluid output manifold 28. Cuvette 26 is supported between fluid input manifold 24 and fluid output manifold 28 which are supported by a frame 29.

Figure 3:
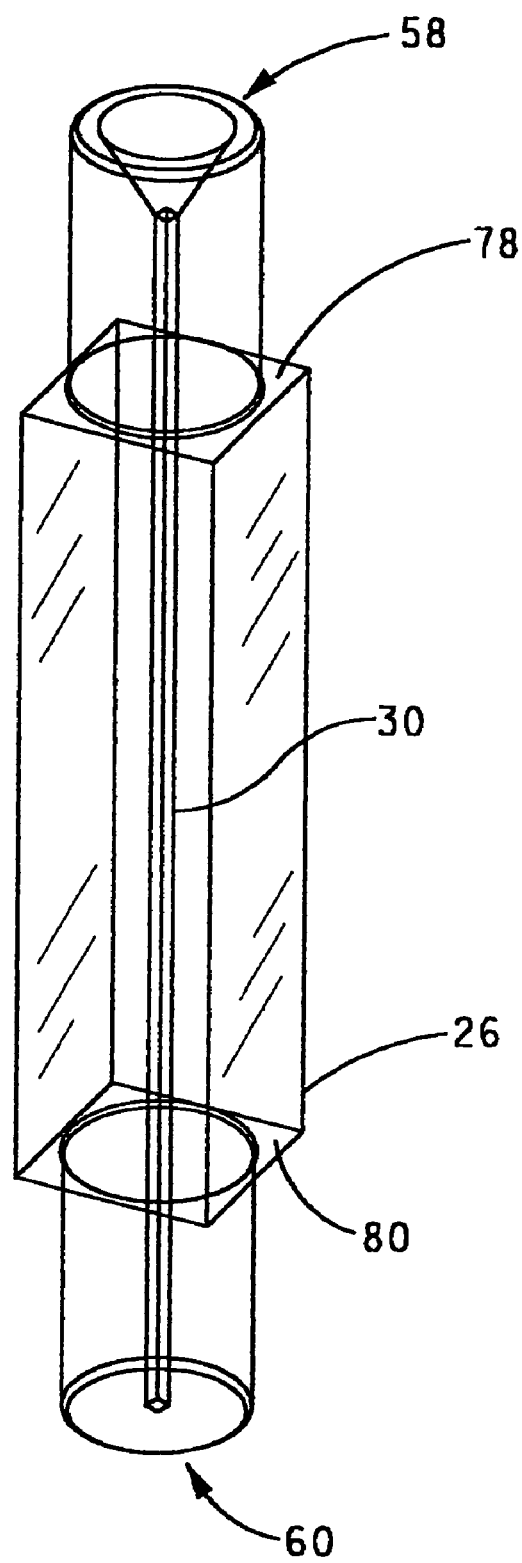
FIG. 3 is an isolated perspective view of a cuvette utilized in the sample flow system shown in FIG. 1.

Desirably, frame 29 supports cuvette 26 relative to lenses 12, 14 and 16 such that focal point 10 of laser light 4 resides within a central bore 30 of cuvette 26, shown best in FIG. 3. Desirably, optical system 8 shapes laser light 4 such that focal point 10 has an elliptical shape, shown best in FIG. 1, with a longitudinal axis thereof positioned within central bore 30 of cuvette 26. Desirably, the longitudinal axis of focal point 10 is oriented perpendicular to the longitudinal axis of cuvette 26.

Interaction of laser light 4 with sample fluid 32 flowing in central bore 30 produces light 34. Light 34 can be comprised of so-called side scatter light produced by the interaction of focal point 10 of laser light 4 with particles in sample fluid 32 and fluorescent light produced by interaction of focal point 10 of laser light 4 with the dye utilized to tag the particles suspended in sample fluid 32.

Light 34 exiting cuvette 26 passes through an optical system 36 which shapes and focuses light 34 and passes the shaped and focused light 34 to a detection means 38 for converting the optically processed light to at least one electrical signal for detection by processing electronics 40.

Desirably, optical system 36 includes a microscope objective lens 42, a spatial filter 43 and relay lens 44 positioned such that light 34 exiting cuvette 26 passes through microscope objective lens 42, spatial filter 43 and relay lens 44. Spatial filter 43 filters unwanted reflections of light 34, whereupon light 34 reaching relay lens 44 contains few or no reflections. In practice, spatial filter 43 can comprise an opaque sheet of material having a small hole therethrough for permitting passage of unreflected light 34 therethrough while blocking the passage of reflected light 34 therethrough.

Light exiting relay lens 44 impinges on a beam splitter 46 whereupon wavelengths of light 34 greater than 665 nm, i.e., fluorescent light, are directed thereby to a band-pass filter 48 and wavelengths of light 34 less than 645 nm, i.e., side scatter light, are directed thereby to a photodetector 54. Band-pass filter 48 filters out any unwanted wavelengths of light 34 below 665 nm and passes the thus filtered light to a photodetector 50. The output of photodetectors 50 and 54 are passed to processing electronics 40 for processing in a manner known in the art.

Desirably, each photodetector 50 and 54 is positioned at a focal point of the light 34 output by optical system 36. The use of beam splitter 46 and photodetectors 50 and 54 facilitates redundant sampling of light 34 by processing electronics 40 whereupon the detection of false readings occasioned by the use of a single photodetector can be avoided.

Desirably, all of the above-described components are operatively mounted on a suitable support structure (not shown). In order to facilitate replacement of cuvette 26, frame 29 can be removed from the support structure. The attachment of input manifold 24 and/or output manifold 28 to frame 29 can then be loosened to facilitate the replacement of cuvette 26 between input manifold 24 and output manifold 28. Once a new cuvette 26 has been installed between input manifold 24 and output manifold 28, the attachment of input manifold 24 and/or output manifold 28 to frame 29 can be tightened and frame 29 subsequently reattached to the support structure.

Desirably, and in accordance with the present invention, lens 16 is physically attached to frame 29 such that when cuvette 26 is replaced, the focal point 10 of laser light 4 can readily be positioned in central bore 30 of the replacement cuvette 26 by adjustment of adjustment stage 20. If adjustment of adjustment stage 20 is insufficient to properly position focal point 10 within central bore 30 of cuvette 26, adjustment stage 18 can be adjusted whereupon the position of lens 14 can be adjusted, thereby adjusting the position of focal point 10. The adjustment of adjustment stage 18 and/or 20 can proceed as necessary until focal point 10 is placed within central bore 30 of cuvette 26. Essentially, adjustment stage 18 is utilized to provide fine adjustment of the position of focal point 10 while adjustment stage 20 is utilized to provide coarse adjustment of the position of focal point 10.

In operation, with focal point 10 of laser light 4 positioned in central bore 30 of cuvette 26, sample fluid 32, containing particles under test that have been tagged with a suitable dye, and a sheath fluid 56 are introduced into central bore 30 via input manifold 24 such that a flow of sample fluid 32 is entrained in non-mixing contact with a flow of sheath fluid 56. The interaction of sample fluid 32 and, more particularly, the particles contained in sample fluid 32 with laser light 4 at focal point 10 produces light 34 which is focused by the optical system 36 and converted into electrical signals by photodetectors 50 and 54 for processing by processing electronics 40.

Figure 2:
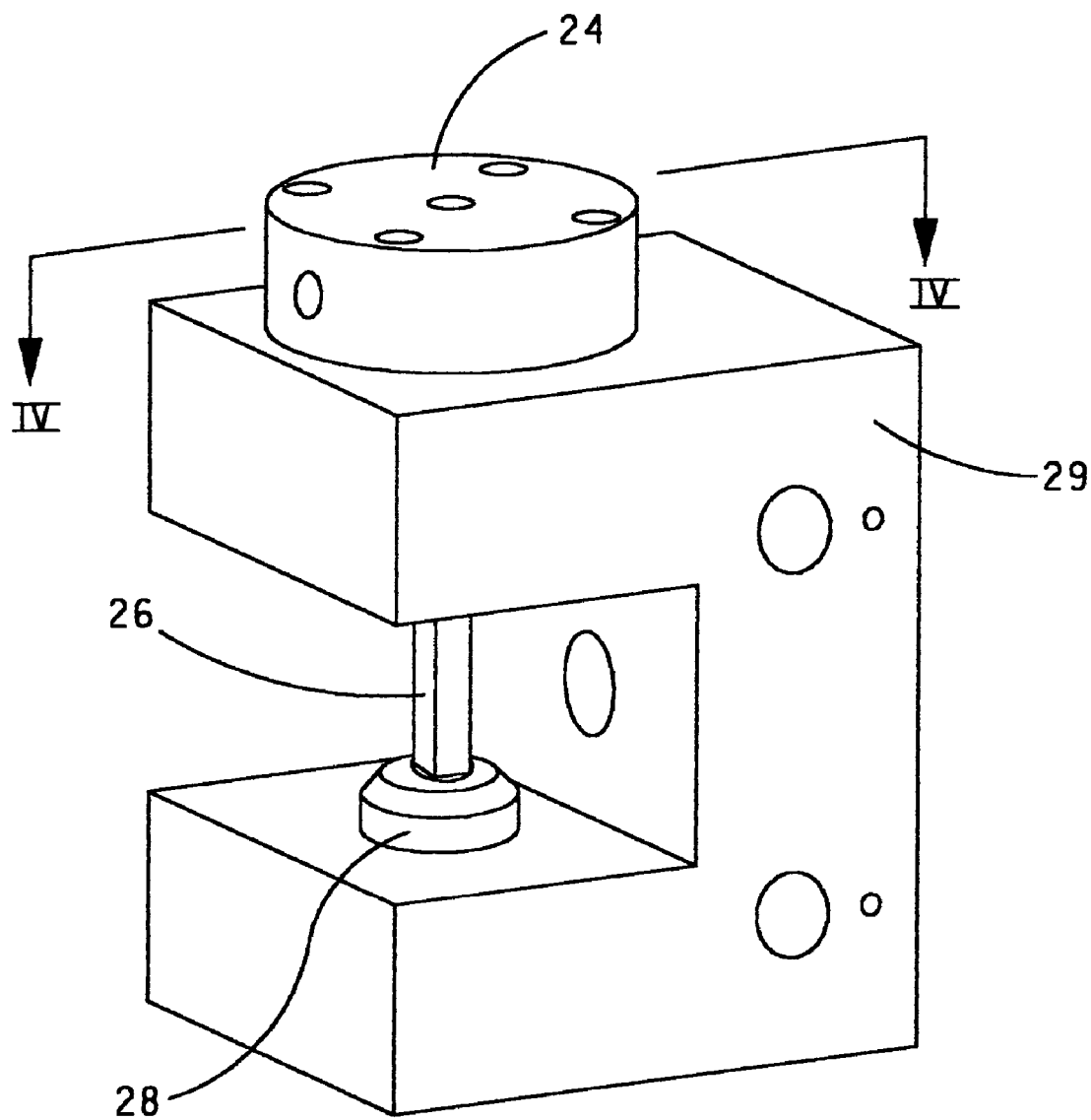
FIG. 2 is an isolated perspective view of an exemplary sample flow system used in the cytometer system shown in FIG. 1.

With reference to FIG. 2 and with continuing reference to FIG. 1, desirably, frame 29 is a unitary frame which supports input manifold 28, cuvette 26 and output manifold 28 in operative relation as shown.

With reference to FIG. 3 and with continuing reference to FIGS. 1 and 2, cuvettes, like cuvette 26, are well known in the art. Exemplary cuvettes are formed from suitable crystalline material, such as quartz or silica. Cuvettes are formed in a manner known in the art such that the central bores thereof, such as central bore 30, have a desired cross sectional shape, such as the square cross section shown in FIG. 3. Prior art cuvettes 26 have central bores 30 that have the same cross sectional shape along their entire length. In accordance with the present invention, however, adjacent first end 58 of cuvette 26, where sample fluid 32 and sheath fluid 56 are received from input manifold 24, central bore 30 has a frustoconical shape with a cross section that gradually diminishes in diameter with increasing distance from first end 58. This gradually diminishing cross-sectional diameter of the frustoconical shaped section of central bore 30 terminates in a section of central bore 30 that has a cross sectional shape, such as, without limitation, a square cross section, that extends therefrom toward a second end 60 of cuvette 26 where fluids received in central bore 30 are discharged from cuvette 26 into discharge manifold 28.

Desirably, cuvette 26 has the exterior shape shown in FIG. 3. However, this is not to be construed as limiting the invention since cuvette 26 can have any suitable and/or desirable exterior shape.

Figure 4:
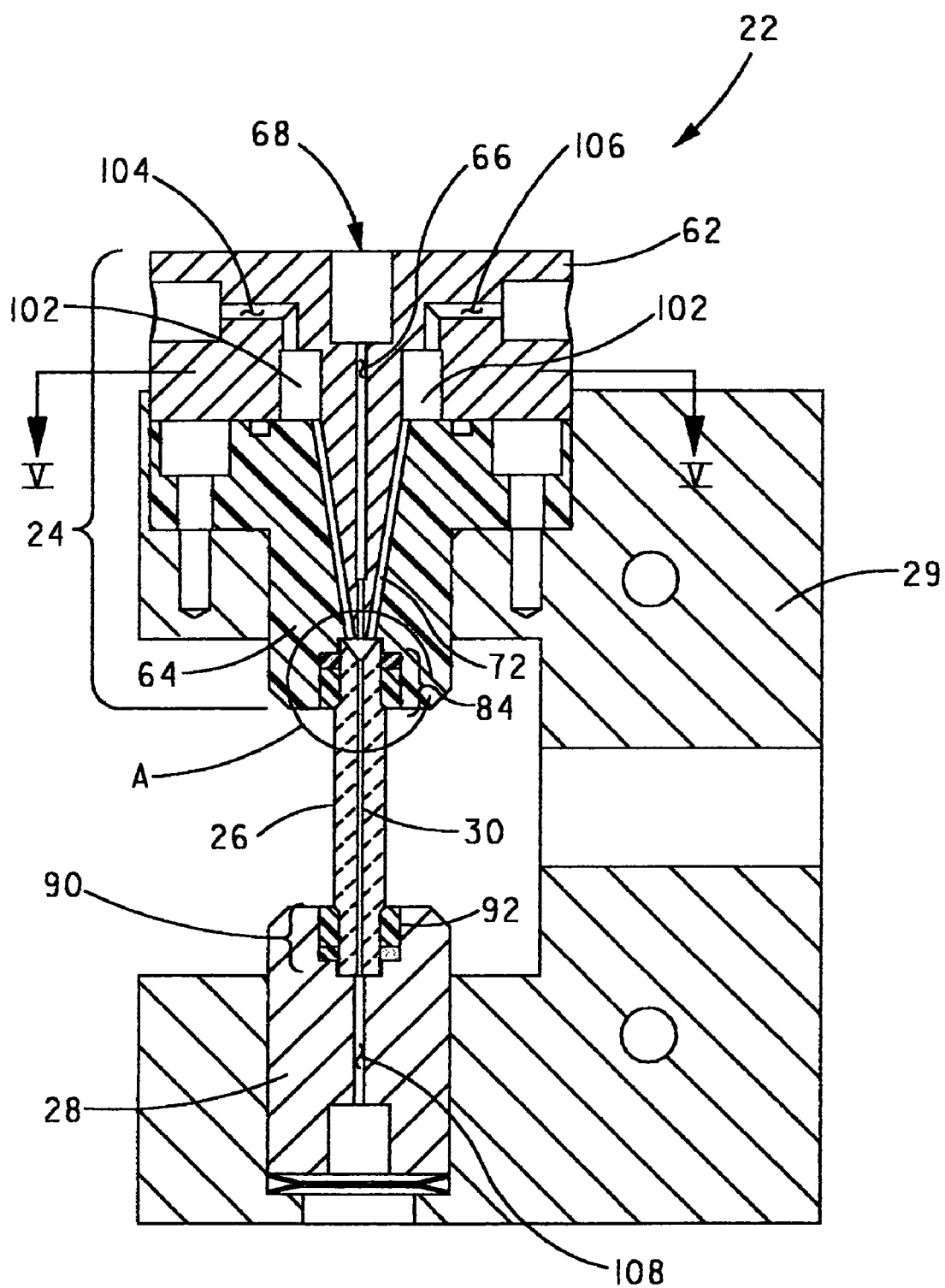
FIG. 4 is a cross section taken along lines IV-IV in FIG. 2.
Figure 5:
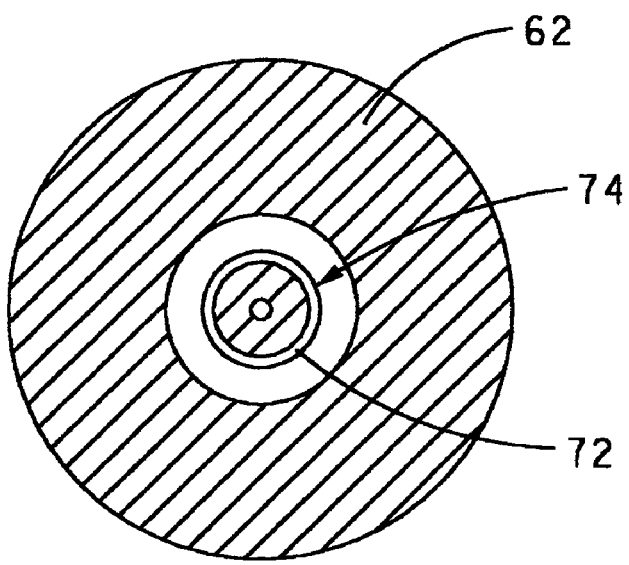
FIG. 5 is a cross section taken along lines V-V in FIG. 4.
Figure 6:
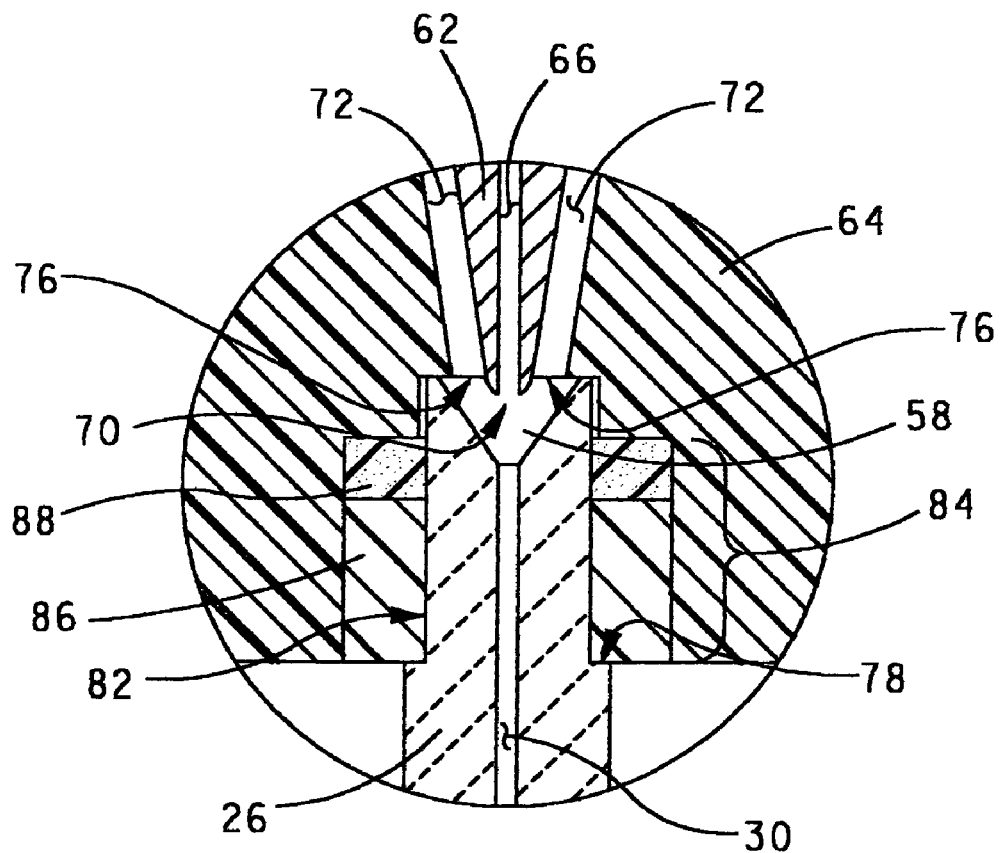
FIG. 6 is an enlarged view of the portion of the sample flow system shown within circle A in FIG. 4.

With reference to FIGS. 4-6 and with continuing reference to FIGS. 1-3, input manifold 24 includes a first body part 62 and a second body part 64. First body part 62 is desirably formed from stainless steel that is coated with a suitable polymer that avoids the accumulation of bacteria on at least each surface of first body part 62 that comes into contact with sample fluid 32 and/or sheath fluid 56. Second body part 64 is desirably formed either entirely from polyetheretherketone (PEEK) or from stainless steel that is coated with a suitable polymer that avoids the accumulation of bacteria on at least each surface of second body part 64 that comes into contact with sample fluid 32 and/or sheath fluid 56. The above-described materials and/or coating forming first body part 62 and second body part 64, however, are not to be construed as limiting the invention.

First body part 62 includes a sample bore 66 having a first end 68 for receiving sample fluid 32 therein, and a second end 70 for discharging received sample fluid 32 into central bore 30 of cuvette 26. First body part 62 also includes an injection chamber 72 surrounding sample bore 66 in spaced relation thereto. Injection chamber 72 includes a first end 74 for receiving sheath fluid 56 therein and a second end 76 for discharging the received sheath fluid 56 into central bore 30 of cuvette 26. Injection chamber 72 has a cross section that gradually decreases in area toward second end 76. Desirably, injection chamber 72 is frustoconical shaped.

As shown best in FIG. 6, first end 58 of cuvette 26 is positioned abutting the material of second body part 64 surrounding second end 76 of injection chamber 72. As shown in FIG. 3, first end 58 and second end 60 of cuvette 26 have circular cross sections. Between first end 58 and second end 60, the exterior surface of cuvette 26 has a square cross section. Cuvette 26 defines a first shoulder 78 at the transition between the square cross-sectional exterior surface of cuvette 26 and the circular cross-sectional exterior surface of square bore 26 adjacent first end 58 thereof. Cuvette 26 also defines a second shoulder 80 at the transition between the square cross-sectional exterior surface of cuvette 26 and the circular cross-sectional exterior surface of cuvette 26 adjacent second end 60 thereof.

Figure 7:
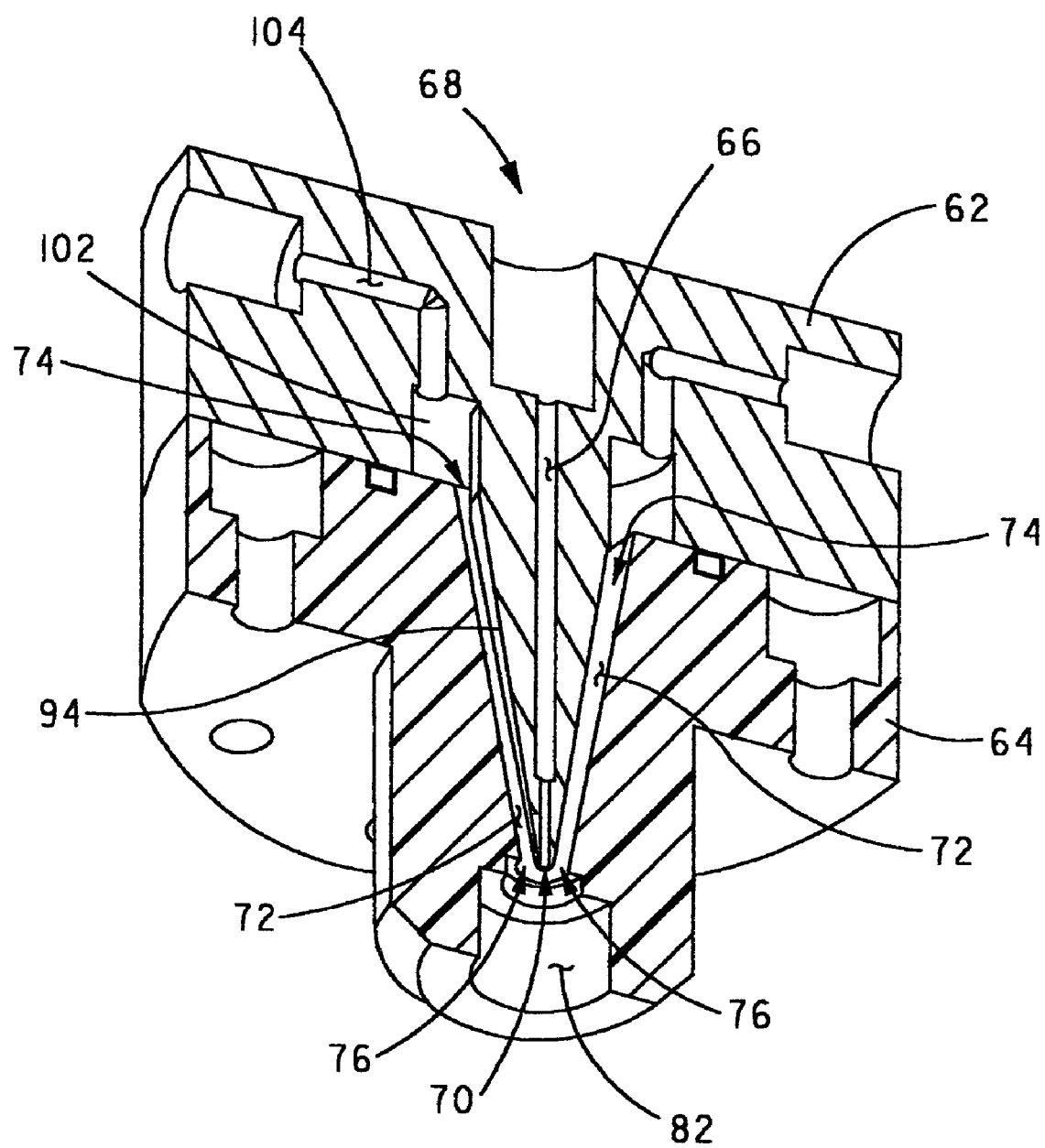
FIG. 7 is an isolated perspective view of the fluid input manifold of the sample flow system shown in FIG. 4.

With reference to FIG. 7 and with continuing reference to FIGS. 1-6, input manifold 24 includes a cylindrical aperture 82 configured to receive first end 58 of cuvette 26. A compression fitting 84, shown best in FIG. 6, is positioned between the exterior surface of cuvette 26 adjacent first end 58 and the cylindrical interior surface of cylindrical aperture 82. Compression fitting 84 includes a ferrule 86 that rests on shoulder 78 of cuvette 26 and a compressible gasket 88, such as an O-ring, positioned on ferrule 86 opposite shoulder 78. Similarly, a compression fitting 90, like compression fitting 84, is positioned between the exterior surface of cuvette 26 adjacent second end 60 and an interior surface of a cylindrical aperture 92 of fluid output manifold 28. When cuvette 26 is assembled between input manifold 24 and output manifold 28 as shown in FIG. 4, compression fittings 84 and 90 act as fluid tight seals to prevent leakage of sample fluid 32 and/or sheath fluid 56 during testing.

Figure 8:
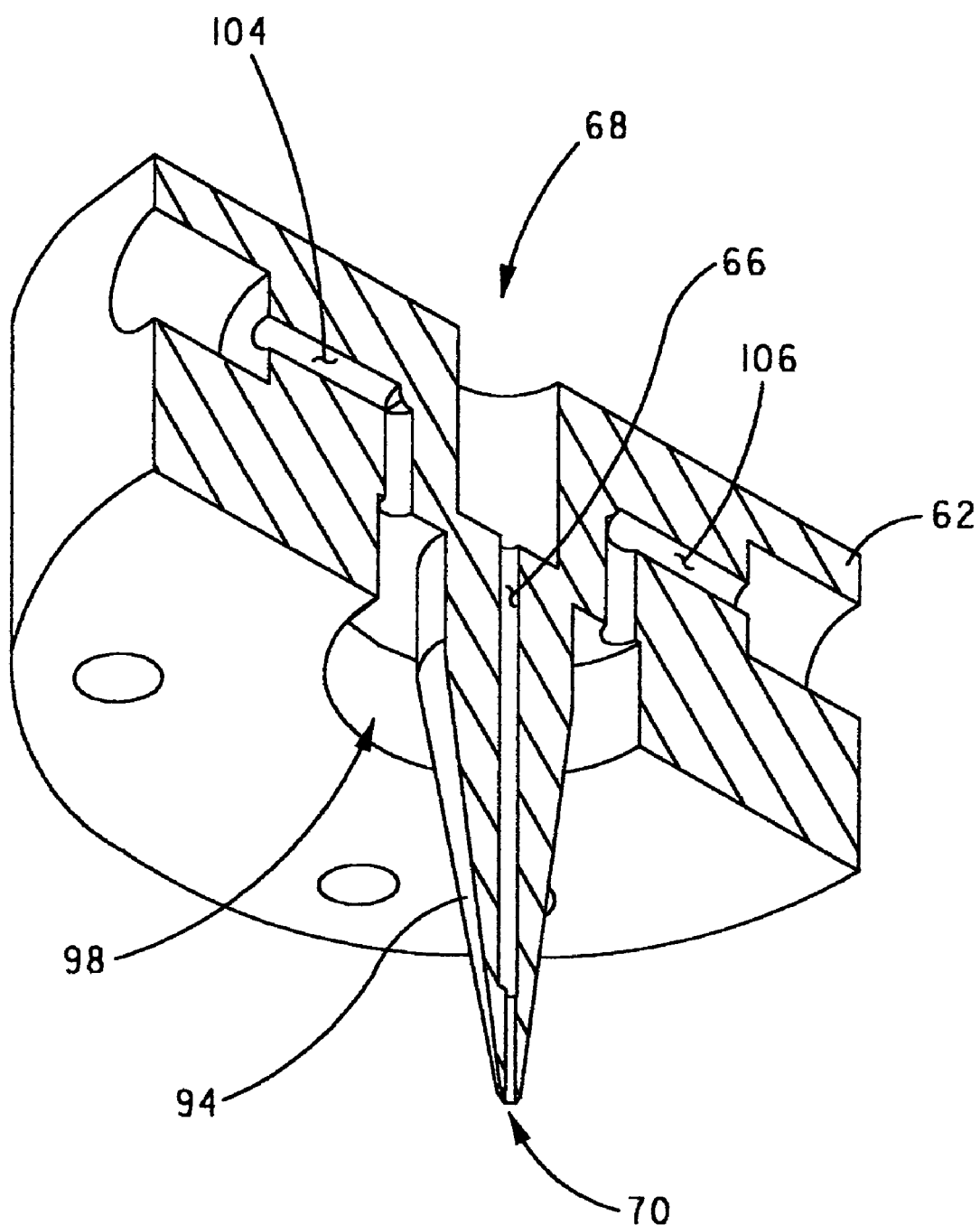
FIG. 8 is an isolated perspective view of a first body part of the fluid input manifold shown in FIG. 7.
Figure 9:
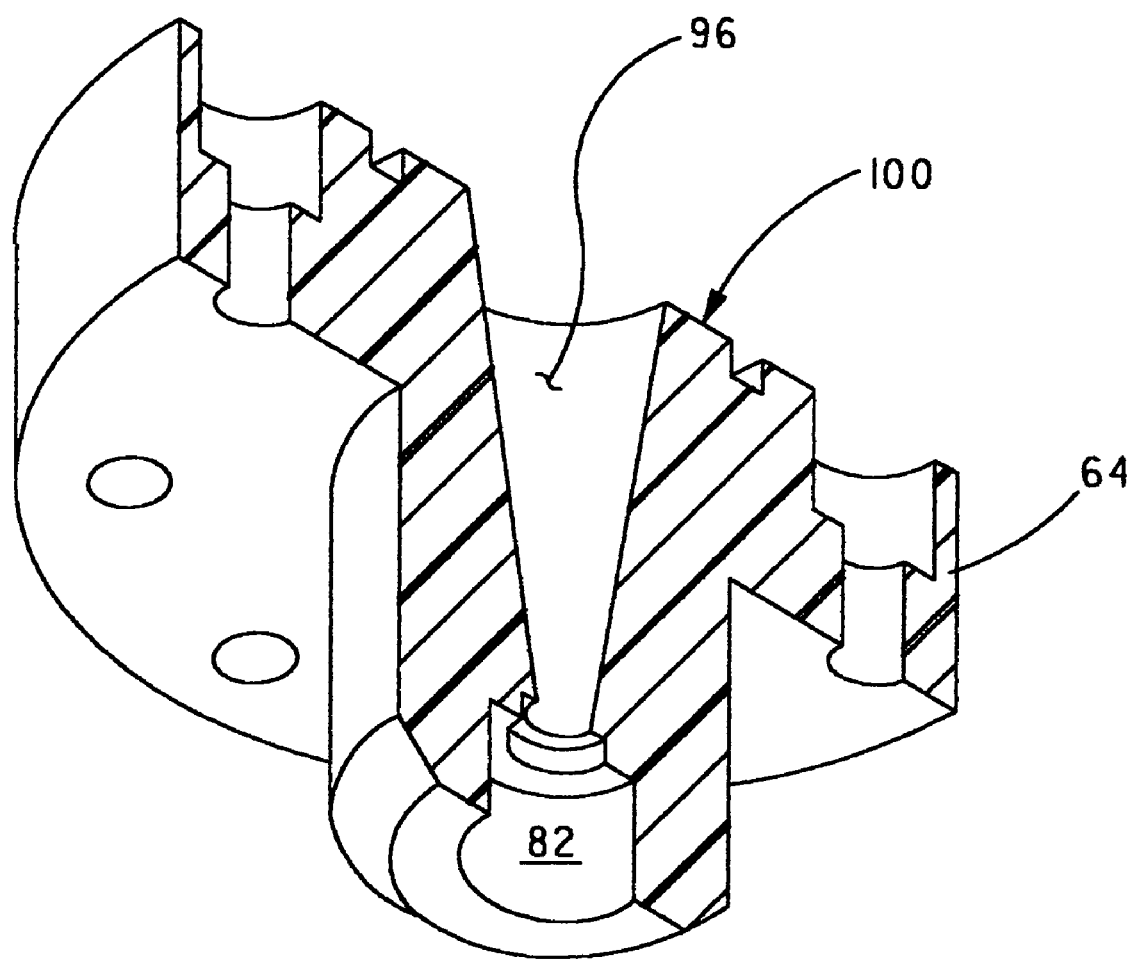
FIG. 9 is an isolated perspective view of a second body part of the fluid input manifold shown in FIG. 7.

With reference to FIGS. 8-9 and with continuing reference to FIGS. 1-7, first body part 62 includes a cone shaped projection 94 extending therefrom. Cone shaped projection 94 includes sample bore 66 extending therethrough, desirably co-axially. Second body part 64 includes a cone shaped aperture 96 therein. As shown in FIG. 7, first body part 62 and second body part 64 are configured to mate such that cone shaped projection 94 is received in spaced relation to cone shaped aperture 96 thereby defining injection chamber 72.

First body part 62 includes a groove 98 formed therein surrounding a base of cone shaped projection 94. When first body part 62 and second body part 64 are mated, a surface 100 of second body part 64 partially covers groove 98 thereby defining a pre-injection chamber 102 that surrounds the base of cone shaped projection 94. As shown best in FIG. 7, pre-injection chamber 102 is in fluid communication with first end 74 of injection chamber 72 adjacent the base of cone shaped projection 94.

First body part 62 includes a passage 104 in fluid communication between groove 98 and a surface of first body part 62 that is not in contact with second body part 64 when first body part 62 and second body part 64 are mated. First body part 62 may also include a passage 106 in fluid communication between groove 98 and a surface of first body part 62 that is not in contact with second body part 64 when first body part 62 and second body part 64 are mated. Passages 104 and 106 can be utilized for a number of different purposes. For example, passage 104 can be utilized to introduce sheath fluid 56 into chamber 102 while passage 106 can be utilized as a vent during the introduction of sheath fluid into pre-injection chamber 102 in order to facilitate the evacuation of bubbles from chamber 102. Passage 104 can also be used as an input for cleaning solution into pre-injection chamber 102, injection chamber 72 and central bore 30 while passage 106 can be used as a drain for any cleaning solution that does not flow into injection chamber 72 and central bore 30.

With reference back to FIG. 4, fluid output manifold 28 includes a discharge bore 108. When input manifold 24, cuvette 26 and output manifold 28 are supported by frame 30 in the manner shown in FIG. 4, sample bore 66, central bore 30 and discharge bore 108 are in alignment.

In use of input manifold 24, cuvette 26 and output manifold 28, sample fluid 32 is introduced into first end 68 of sample bore 66 by any suitable means, such as by a syringe, that desirably controls the rate that sample fluid 32 is introduced into first end 68 of sample bore 66. For example, the cytometer system shown in FIG. 1 can include a suitable mechanism (not shown) for positioning a discharge end of a disposable syringe containing sample fluid 32 in first end 68 of sample bore 66. Thereafter, a suitable mechanical activator (not shown) of the cytometer system can depress the piston of the disposable syringe at a controlled rate thereby discharging sample fluid 32 into sample bore 66 at a desirable rate. Once used, the disposable syringe can be discarded to avoid contamination of other fluid samples.

At the same time sample fluid 32 is being introduced into sample bore 66, sheath fluid 56 is introduced into pre-injection chamber 102 via passage 104 or passage 106. Because chamber 102 has a larger cross-sectional area than first end 74 of injection chamber 72, chamber 102 acts as a reservoir for sheath fluid 56 gradually draining into injection chamber 72 at a controlled rate. Sample fluid 32 exiting second end 70 of sample bore 66 is entrained in non-mixing contact with sheath fluid 56 exiting second end 76 of injection chamber 72. Sample fluid 32 exiting sample bore 66 and sheath fluid 56 exiting injection chamber 72 enter first end 58 of cuvette 26.

To avoid disruption of the flow of sheath fluid 56 exiting injection chamber 72 and entering central bore 30 of cuvette 26, the second end 76 of injection chamber 72 has an outside diameter that is the same as an outside diameter of first end 58 of central bore 30 of cuvette 26 where sheath fluid 56 enters cuvette 26. This is shown best in FIG. 6.

Sample fluid 32 surrounded in non-mixing contact with sheath fluid 56 entering the frustoconical shaped portion of cuvette 26 flows entrained in non-mixing contact through the central portion of central bore 30 and is discharged therefrom into discharge bore 108 of output manifold 28. The combination of sample fluid 32 and sheath fluid 56 exiting discharge bore 108 is either further processed or discharged in a manner known in the art.

The present invention has been described with reference to the preferred embodiment. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A cytometer system comprising:
   a liquid input manifold including:
   a sample bore having a first end for receiving a sample liquid therein and a second end for discharging the received sample liquid; arid
   a pre-injection chamber surrounding the sample bore adjacent the first end thereof in spaced coaxial relation, said pre-injection chamber for receiving sheath liquid therein;
   an injection chamber surrounding the sample bore in spaced coaxial relation, said injection chamber having a first end for receiving sheath liquid therein from said pre-injection chamber and a second end for discharging the received sheath liquid adjacent the second end of the sample bore, said injection chamber having a cross section that gradually decreases in area toward the second end thereof, wherein, where said pre-injection chamber intersects the first end of the injection chamber, said pre-injection chamber has a larger cross-sectional area than the first end of the injection chamber whereupon sheath liquid received in the pre-injection chamber gradually drains into the injection chamber; and
   an elongated cuvette including a central bore having a first end positioned for receiving from the input manifold a flow of sample liquid surrounded by a flow of sheath liquid and a second end for discharging said received liquids, the first end of said central bore having a cross section that gradually diminishes in diameter with increasing distance from said first end, said gradually diminishing cross section diameter of said central bore terminating in a length of said central bore that extends toward the second end of said central bore.

2. The system of claim 1, wherein the input manifold has two surfaces positioned in spaced relation to define the injection chamber.

3. The system of claim 2, wherein the injection chamber is frustoconical shaped.

4. The system of claim 3, wherein the liquid input manifold includes:
   a first body part having a cone shaped projection extending therefrom, said cone shaped projection having said sample bore extending therethrough; and
   a second body part having a cone shaped aperture therein, wherein the first and second body parts are configured to mate such that said cone shaped projection is received in spaced relation to said cone shaped aperture thereby defining the injection chamber.

5. The system of claim 4, wherein:
   the first body part includes therein a groove surrounding a base of said cone shaped projection; and when the first and second body parts are mated, a surface of the second body part partially covers said groove thereby defining the pre-injection chamber that surrounds the base of said cone shaped projection.

6. The system of claim 5, wherein the first body part includes at least one passage in liquid communication between said groove and a surface of the first body part that is not in contact with the second body part when the first and second body parts are mated.

7. The system of claim 4, wherein the sample bore is in liquid communication with a surface of the first body part that is not in contact with the second body part when the first and second body parts are mated.

8. The system of claim 1, wherein the second end of the injection chamber has an outside diameter that is smaller than an outside diameter of the first end of said central bore of said cuvette.

9. The system of claim 1, further including a liquid output manifold having a discharge bore for passage of liquids discharged from the central bore of the cuvette.

10. The system of claim 9, further including a frame for supporting the input manifold and the output manifold with the cuvette therebetween such that the sample bore of the input manifold, the central bore of the cuvette and the discharge bore of the output manifold are in alignment.

11. The system of claim 10, further including:
a first compression fitting between the first end of the cuvette and the input manifold, said first compression fitting forming a liquid tight seal between the input manifold and the first end of the cuvette; and
a second compression fitting between the second end of the cuvette and the output manifold, said second compression fitting forming a liquid tight seal between the output manifold and the second end of the cuvette.

12. The system of claim 1, further including:
means for producing a beam of monochromatic light; and
an optical system for directing and shaping the beam of light such that its focal point is positioned in a flow of sample liquid surrounded by a flow of sheath liquid in the sample bore.

13. The system of claim 12, wherein the focal point has an elongated shape that is oriented perpendicular to a direction of flow of the sample liquid.

14. The system of claim 12, wherein the optical system includes:
a first lens positioned in a path of the beam of monochromatic light;
a focusing lens positioned in the beam of monochromatic light exiting said first lens; and
means for adjusting a position of at least one of the first lens and the focusing lens to adjust the position of the focal point of the beam of light.

15. The system of claim 12, further including:
a second optical system for focusing light resulting from the interaction of the beam of light with the sample liquid; and
means for converting the focused light into at least one electrical signal for detection by processing electronics.

16. The system of claim 15, wherein:
the second optical system includes at least one lens for focusing the light produced by the interaction of the shaped beam of light with the sample liquid and a spatial filter for filtering the focused light to remove undesirable reflections therefrom; and
the means for converting the focused light includes at least one photodetector.

17. The system of claim 16, further including a beam splitter for directing a first wavelength of focused light to a first photodetector and for directing a second wavelength of focused light to a second photodetector via a band-pass filter which is configured to remove undesirable wavelengths of focused light that accompany the second wavelength of the focused light.

18. A cytometer system comprising:
a liquid input manifold comprising a sample bore for accommodating a flow of sample liquid surrounded by a frustoconical shaped chamber for accommodating a flow of sheath liquid received from a pre-injection chamber that surrounds the sample bore adjacent one end thereof; and
a cuvette including a central bore positioned for receiving from the input manifold the flow of the sample liquid surrounded by and in non-mixing contact with the flow of the sheath liquid, the section of the central bore receiving the sample liquid and the sheath liquid having a frustoconical shape, said frustoconical shaped section converging with increasing distance from where the flow of the sample liquid surrounded by the flow of the sheath liquid is received in the central bore, wherein:
the pre-injection chamber is in liquid communication with an end of the frustoconical shaped chamber opposite the cuvette; and
at an intersection between said pre-injection chamber and the end of the frustoconical shaped chamber opposite the cuvette, said pre-injection chamber has a larger cross-sectional area than the end of the frustoconical shaped chamber opposite the cuvette whereupon sheath liquid input into the pre-injection chamber gradually drains into the end of the frustoconical shaped chamber opposite the cuvette.

19. The system of claim 18, wherein:
sheath liquid exits the frustoconical shaped chamber adjacent the end thereof that has a minimum outside diameter and enters the frustoconical shaped section of the central bore adjacent the end thereof that has a maximum outside diameter; and
the maximum outside diameter of the frustoconical shaped section of the central bore is the same as the minimum outside diameter of the frustoconical shaped chamber.

20. The system of claim 18, wherein at least one of the sample liquid and the sheath liquid is introduced into the input manifold at a controlled rate.

21. The system of claim 18, further including a disposable syringe operative for introducing the sample liquid into the sample bore.

* * * * *

UNITED STATES PATENT AND TRADEMARK OFFICE
CERTIFICATE OF CORRECTION

PATENT NO. : 7,468,789 B2  Page 1 of 1
APPLICATION NO. : 11/051871
DATED : December 23, 2008
INVENTOR(S) : Robert Czarnek It is certified that error appears in the above-identified patent and that said Letters Patent is hereby corrected as shown below:

<u>Title page</u>, Item (56) References Cited, U.S. PATENT DOCUMENTS, insert the following two U.S. patents:
--     5,030,002     09/1991     North, Jr. --
--     7,105,355     09/2006     Kurabayashi et al. --

<u>Column 8</u>, Line 22, Claim 1, "liquid; arid" should read -- liquid; and --

Signed and Sealed this

Fifth Day of May, 2009

JOHN DOLL
*Acting Director of the United States Patent and Trademark Office*